(12) United States Patent
Pianca et al.

(10) Patent No.: US 7,450,997 B1
(45) Date of Patent: Nov. 11, 2008

(54) METHOD OF IMPLANTING A LEAD FOR BRAIN STIMULATION

(75) Inventors: Anne M Pianca, Valencia, CA (US); Carla Mann Woods, Beverly Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 372 days.

(21) Appl. No.: 11/379,719

(22) Filed: Apr. 21, 2006

Related U.S. Application Data

(62) Division of application No. 10/035,745, filed on Dec. 28, 2001, now Pat. No. 7,033,326.

(60) Provisional application No. 60/258,767, filed on Dec. 29, 2000.

(51) Int. Cl.
*A61N 1/05* (2006.01)

(52) U.S. Cl. ............... 607/116; 600/378; 128/898; 128/899; 606/129; 606/130

(58) Field of Classification Search ............... 606/129, 606/130; 607/116; 600/585, 378, 544; 128/898, 128/899
See application file for complete search history.

(56) References Cited

U.S. PATENT DOCUMENTS

| | | | | |
|---|---|---|---|---|
| 5,116,345 | A * | 5/1992 | Jewell et al. | 606/130 |
| 6,413,263 | B1 * | 7/2002 | Lobdill et al. | 606/129 |
| 6,799,074 | B1 * | 9/2004 | Thomas et al. | 607/116 |
| 2001/0014820 | A1 * | 8/2001 | Gielen et al. | 607/116 |

* cited by examiner

*Primary Examiner*—Kennedy J Schaetzle
(74) *Attorney, Agent, or Firm*—Darby & Darby, P.C.

(57) ABSTRACT

Leads and introduction tools are proposed for deep brain stimulation and other applications. Some embodiments of the present invention provide lead designs with which may be placed with a stylet, while others do not require a stylet. Some lead embodiments use standard wire conductors, while others use cable conductors. Several embodiments incorporate microelectrodes and/or microelectrode assemblies. Certain embodiments of the present invention provide introduction tools, such as cannula and/or cannula systems, which ensure proper placement of, e.g., leads.

7 Claims, 10 Drawing Sheets

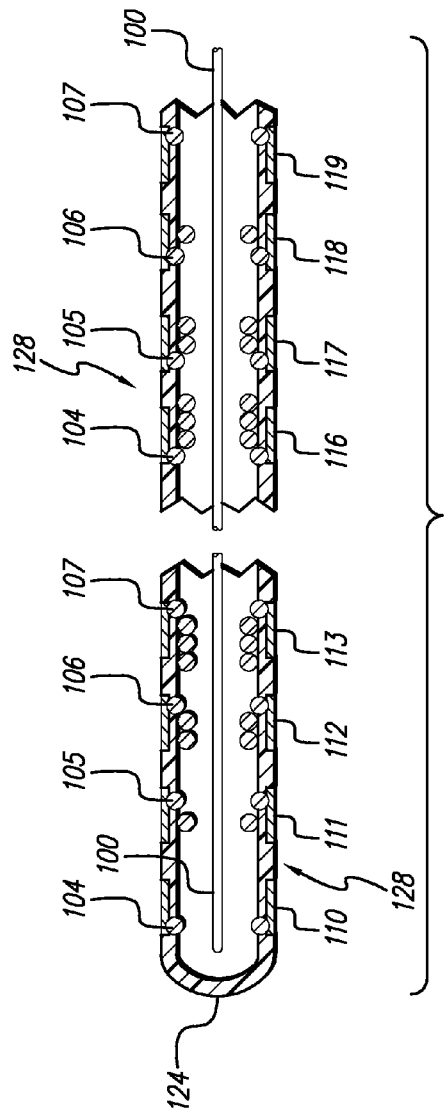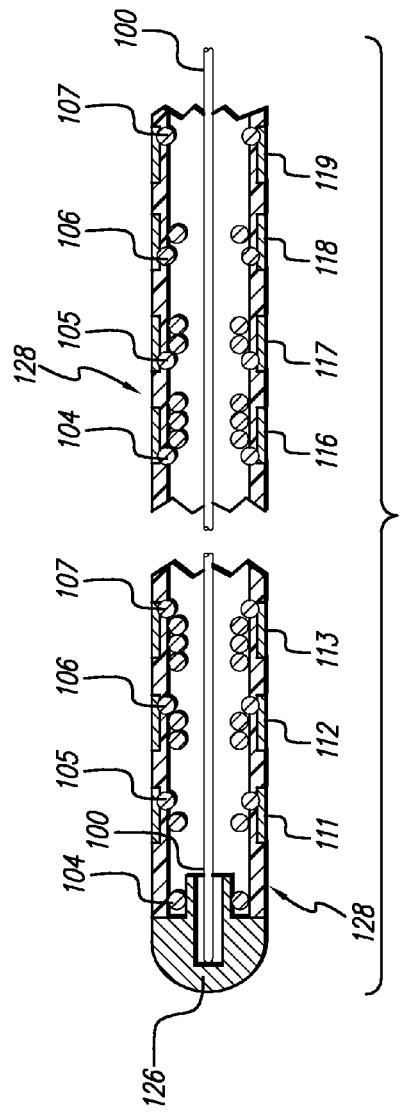

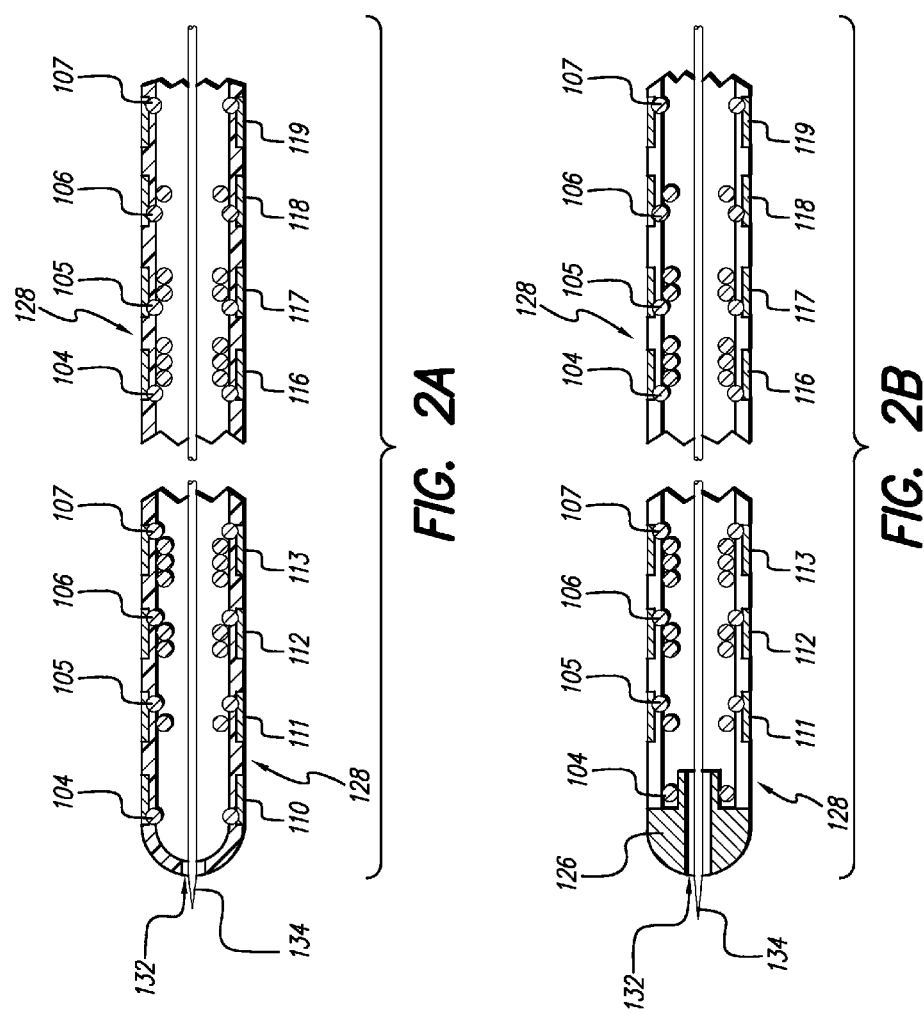

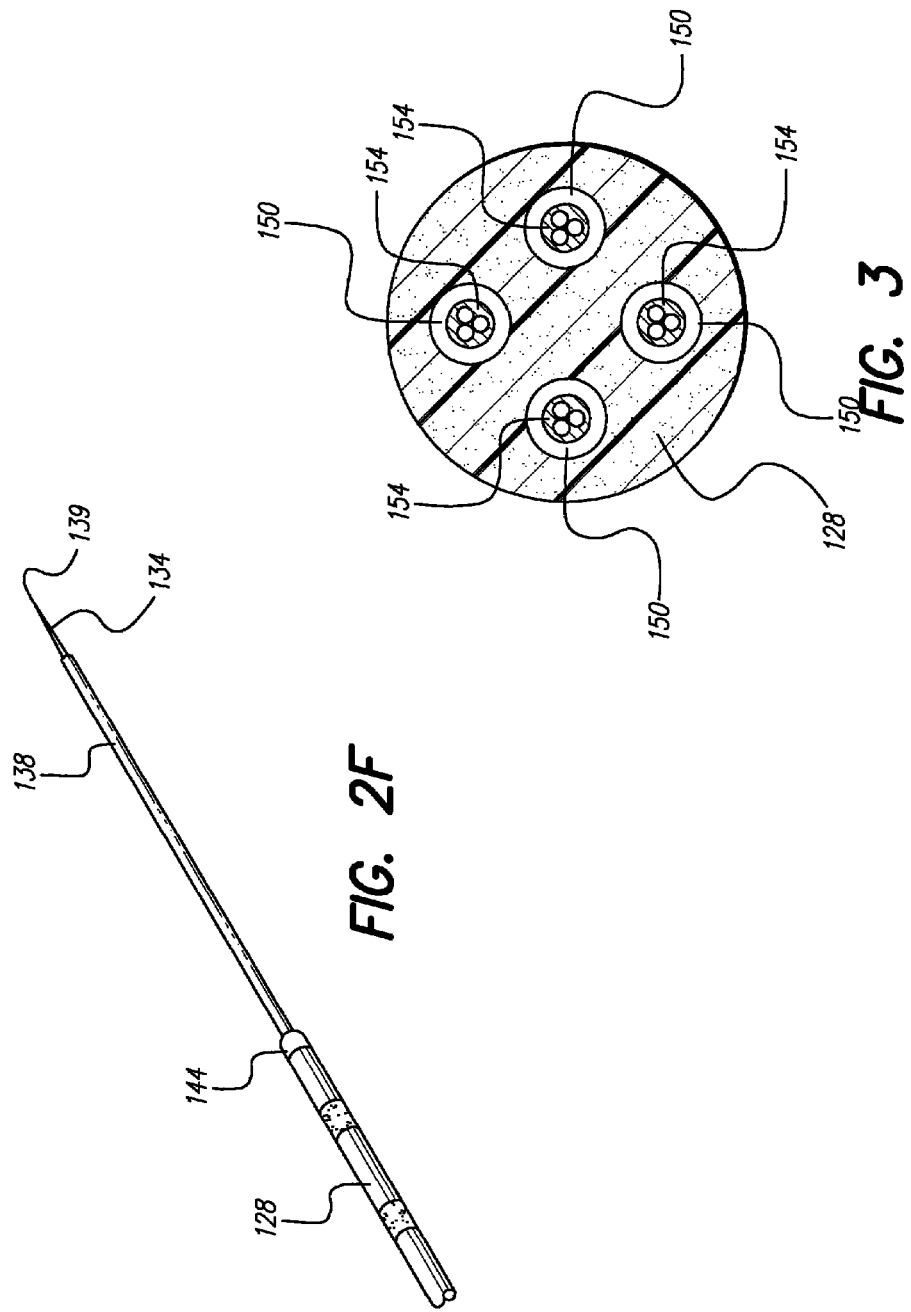

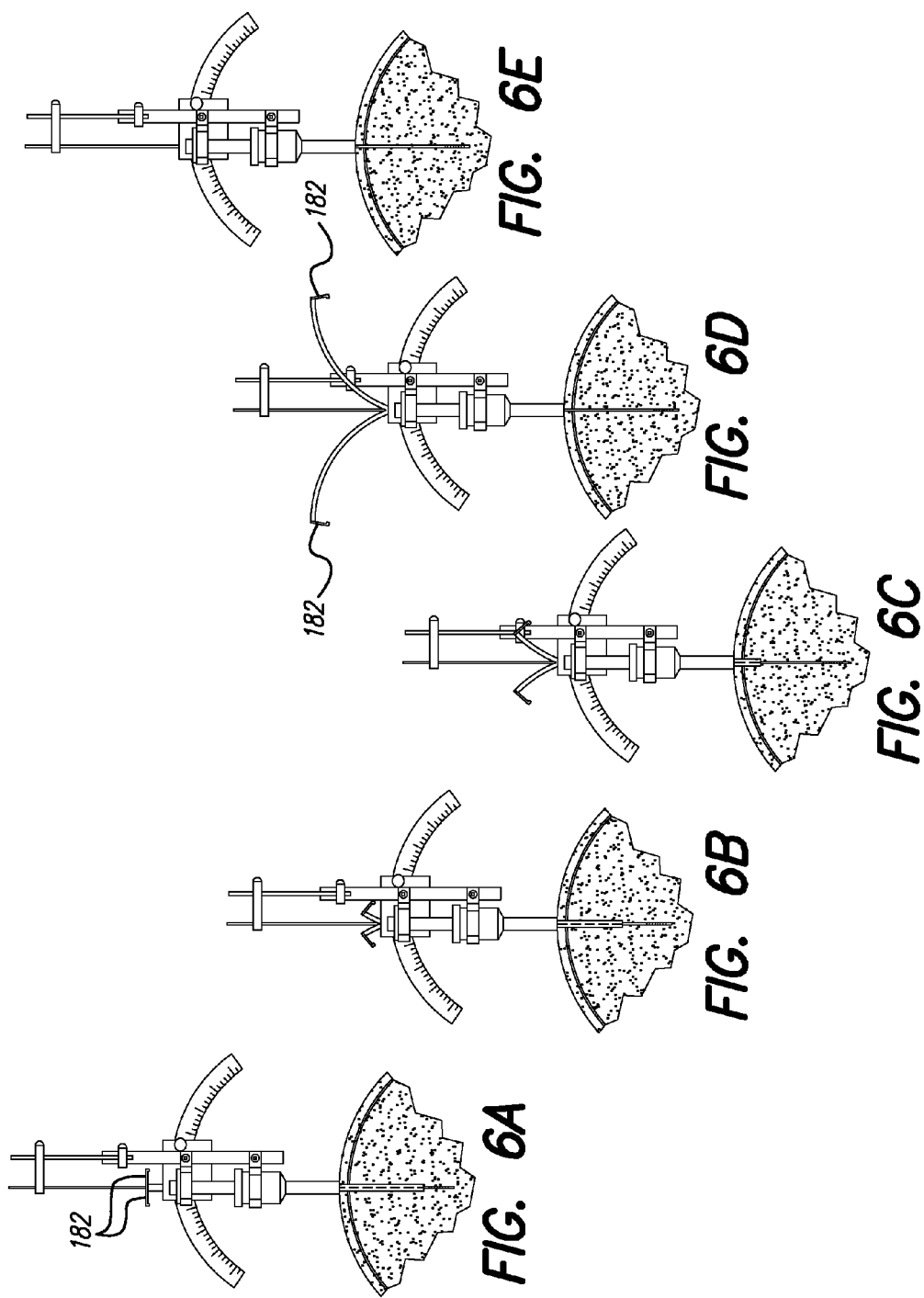

METHOD OF IMPLANTING A LEAD FOR BRAIN STIMULATION

The present application is a Divisional of application Ser. No. 10/035,745, filed Dec. 28, 2001, to be issued as U.S. Pat. No. 7,033,326 on Apr. 25, 2006 which application claims the benefit of U.S. Provisional Patent Application Ser. No. 60/258,767, filed Dec. 29, 2000, which applications and patent are incorporated herein by reference.

FIELD OF THE INVENTION

The present invention generally relates to medical leads and systems, and more particularly relates to lead systems and methods of introducing leads for brain or other stimulation.

BACKGROUND OF THE INVENTION

Deep brain stimulation (DBS) in the thalamus for the treatment of tremor was approved by the FDA in 1997. Subsequently, it has been found that stimulation in various areas of the brain may be useful for treating a variety of conditions, including providing relief from symptoms of Parkinson's disease and other diseases.

In July 2001, the National Institute of Neurological Disorders and Stroke and the National Institute of Mental Health reported that over two thousand patients have been implanted with DBS systems, and that the number was growing rapidly. Using current guidelines, estimations are that as many as 15,000 individuals per year may be candidates for this procedure. This number could increase as the population ages and/or if the indications are expanded.

SUMMARY OF THE INVENTION

The invention disclosed and claimed herein provides advances in leads and introduction tools which are useful in deep brain stimulation and other applications. Some embodiments of the present invention provide lead designs with a tip electrode, some with an insulating material at the distal tip, and these tips may be rounded. Some of these leads may be placed with a stylet, while others do not require a stylet. Certain lead embodiments have a through-hole that allows the lead and a microelectrode to be advanced and retracted in relation to one another. Some lead embodiments use standard single-wire conductors, while others use cable (i.e., multi-strand or multi-wire) conductors. In some embodiments, the cable conductors make the stylet and stylet lumen unnecessary. Other embodiments provide various lead shapes. Additional embodiments of the present invention provide introduction tools, such as cannula and/or cannula systems.

The leads and introduction tools of the present invention may be used wherever an electrical lead is required, or wherever a similarly shaped item, such as a catheter or a chronic DBS lead, is introduced into a body.

BRIEF DESCRIPTION OF THE DRAWINGS

The above and other aspects of the present invention will be more apparent from the following more particular description thereof, presented in conjunction with the following drawings wherein:

FIG. 1A is an axial cross-section view of one embodiment of a lead of the present invention;

FIG. 1B depicts a variation on the lead of FIG. 1A;

FIG. 2A is an axial cross-section view of another embodiment of a lead of the present invention;

FIG. 2B depicts a variation on the lead of FIG. 2A;

FIG. 2F shows the microelectrode advanced beyond the distal tip of the lead;

FIG. 3 is a cross-section view of another embodiment of a lead of the present invention;

FIGS. 6A-6E depict a method of removing a cannula of a cannula system of the present invention.

Corresponding reference characters indicate corresponding components throughout the several views of the drawings.

DETAILED DESCRIPTION OF THE INVENTION

Figure 2C:
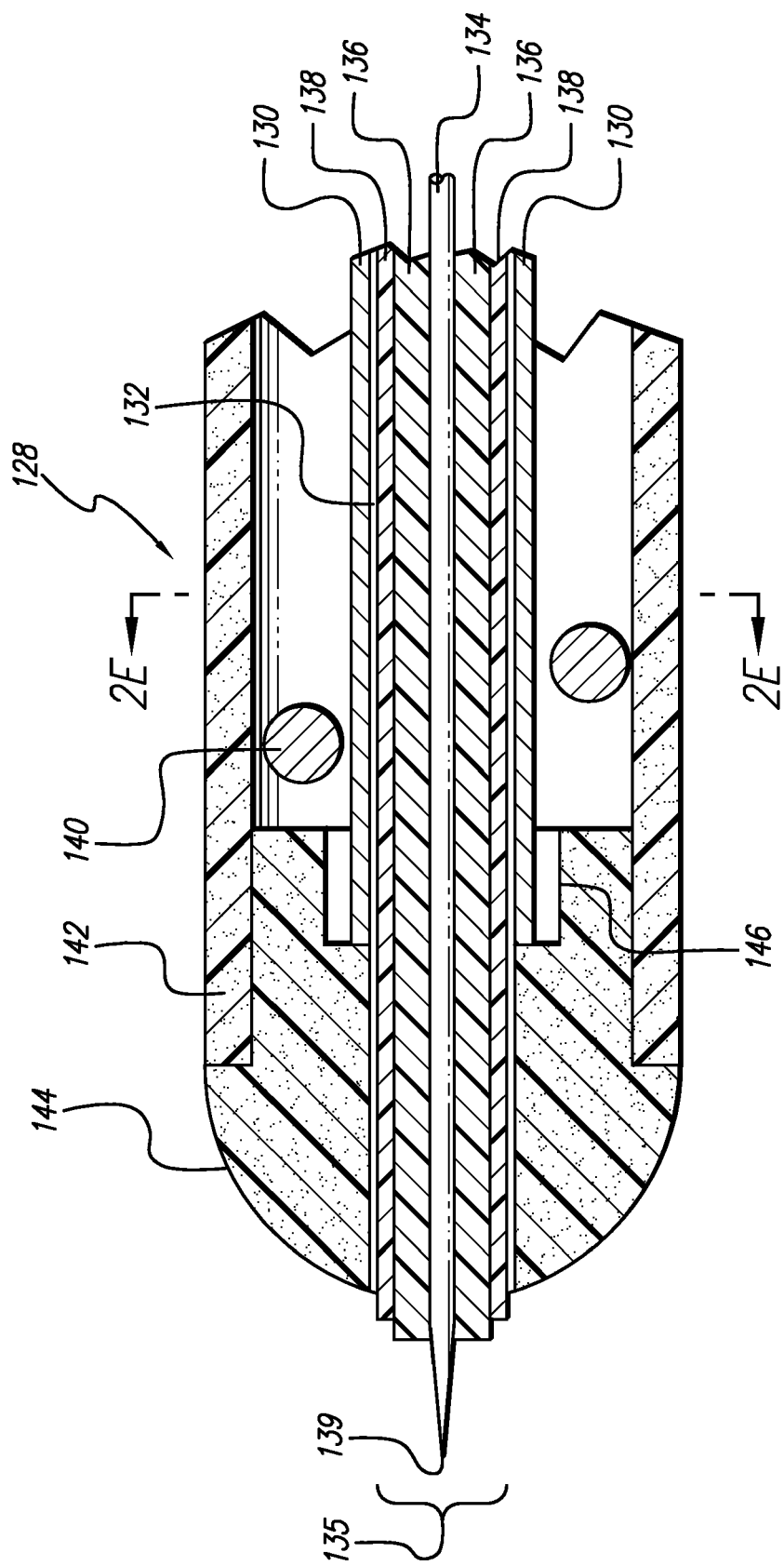
FIG. 2C is a close-up axial cross-section view of the distal tip of a recording microelectrode and another lead embodiment of the present invention.
Figure 2E:
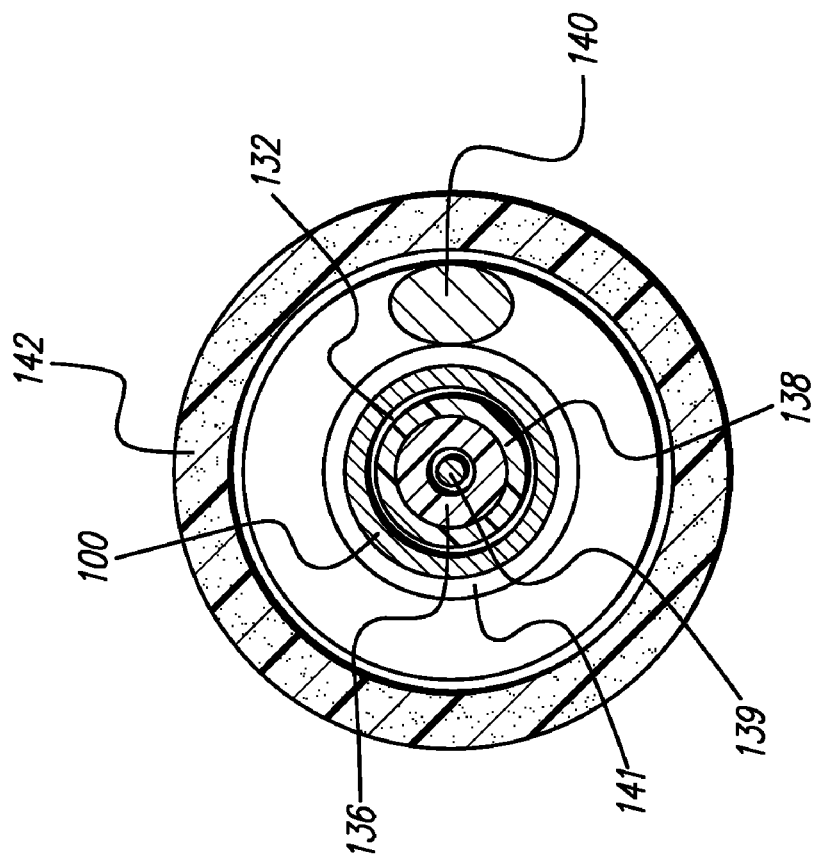
FIG. 2E is a cross-section view of the lead of FIG. 2C.
Figure 2D:
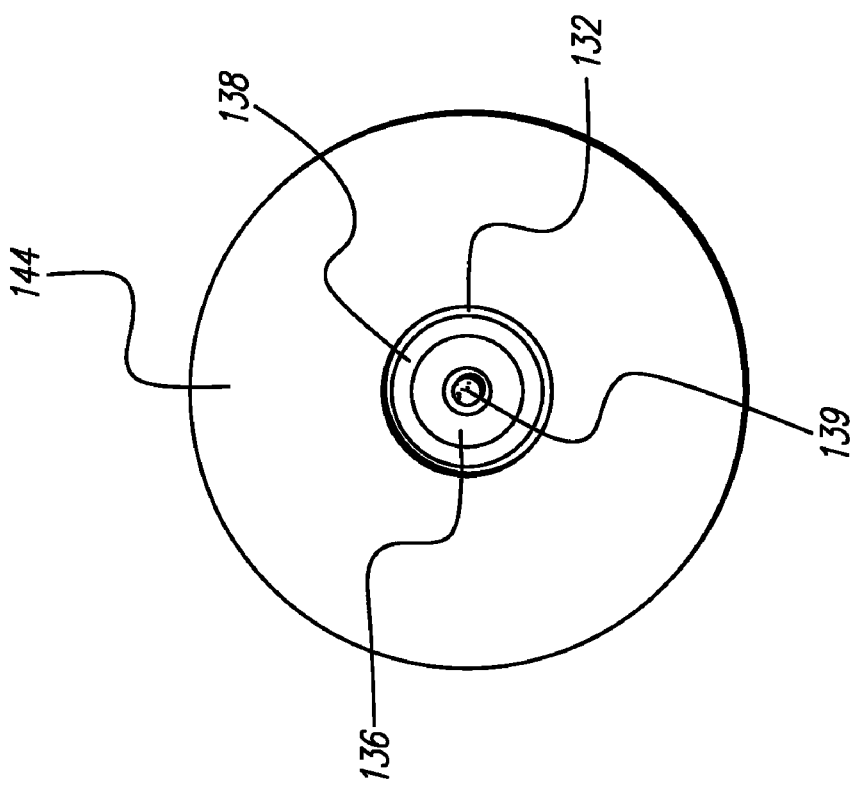
FIG. 2D is an end view of the lead and microelectrode of FIG. 2C.

The following description is of the best mode presently contemplated for carrying out the invention. This description is not to be taken in a limiting sense, but is made merely for the purpose of describing the general principles of the invention. The scope of the invention should be determined with reference to the claims.

Traditional procedures for implanting a permanent brain stimulating or deep brain stimulating (DBS) lead involve several steps, which generally include the following.

1. Place the stereotactic frame on the subject.
2. Perform MRI or equivalent imaging of subject with stereotactic frame.
3. Identify a theoretical target using planning software.
4. Place subject with stereotactic frame in head rest.
5. Cut skin flap, exposing working surface area of cranium using scalp clips.
6. Place stereotactic arc with target coordinate settings and identify location on skull for creation of burr hole.
7. Remove arc and drill a burr hole in the patient's skull.
8. Place the base of the lead anchor.
9. With the microelectrode recording drive attached, and with the appropriate stereotactic frame adaptor inserted into the instrument guide, place the stereotactic arc.
10. Advance a microelectrode cannula and insertion rod into the brain until they are approximately 25 mm above the target.
11. Remove the insertion rod, leaving the cannula in place.
12. Insert the recording microelectrode such that the tip of the microelectrode is flush with the tip of the microelectrode cannula.
13. Attach a connector pin of the recording microelectrode to the microelectrode recording system.
14. Starting approximately 25 mm above the target, begin the microelectrode recording tract using the microdrive to advance the microelectrode at a specified rate.
15. If the target is identified, proceed to step 16. If the target is not identified, proceed with the following:
    a. Using the recording results and the pre-operative imaging, determine a new set of coordinates for the theoretical target.

b. Disconnect the recording microelectrode from the microelectrode recording system.

c. Remove the recording microelectrode cannula and recording microelectrode.

d. Adjust the coordinates of the stereotactic frame.

e. Continue at step 10, above.

16. Remove the recording microelectrode cannula and recording microelectrode.

17. Insert a macroelectrode insertion cannula and rod until they are approximately 25 mm above the target.

18. Remove the insertion rod, leaving the macroelectrode insertion cannula in place.

19. Insert a stimulating macroelectrode, and advance to the target stimulation site identified by the recording microelectrode.

20. Using macrostimulation, simulate the stimulation of the chronic DBS lead to ensure proper response.

21. Remove the macroelectrode and cannula.

22. Insert a DBS lead insertion cannula and an insertion rod, and advance to approximately 25 mm above the stimulation site.

23. Remove the insertion rod.

24. Insert the DBS lead, with stylet, through the insertion cannula, and advance to the stimulation site.

25. Connect the connector of the lead to a trial stimulator.

26. Perform the desired stimulation and measurements using any one or combination of four electrodes on the DBS lead.

27. If the results are favorable, proceed to step 29. If the results are not favorable, proceed with the following:

a. Using the macrostimulation results, microelectrode recording results, and pre-operative imagining, determine a new set of coordinates for the theoretical target.

b. Remove the lead and stylet.

c. Remove the insertion cannula.

d. Adjust the coordinates of the stereotactic frame.

e. Continue at step 10, above.

28. Remove the stylet, followed by the insertion cannula.

29. Using macrostimulation, verify that micro-dislodgement of the DBS lead has not occurred.

30. Lock the DBS lead in the lead anchor.

Some physicians might use additional steps, fewer steps, and/or perform the steps in a different order. Obviously, many of these steps cannot be avoided. However, it would be useful if several of these steps could be combined to minimize the total procedure time.

Another problem associated with the standard DBS lead implant procedure summarized above is micro-dislodgment of the DBS lead when the lead introduction tools are removed. Implant location is critical with traditional DBS leads, as a few microns in lead movement can make the difference between functional and non-functional stimulus therapy. For this reason, a straight DBS lead is sometimes implanted with approximately two electrodes positioned beyond the target location. These electrodes may be able to provide useful stimulation if the lead is pulled in a proximal direction during removal of the introduction tools. Otherwise, repositioning of the lead may be necessary, with the attendant increased risks and expenses. Therefore, systems and methods to eliminate or minimize micro-dislodgement of the DBS lead would also be useful.

In addition, the size and number of holes made in the skull and brain should be minimized. Minimizing either or both the size of holes and/or the repositioning rate lowers the chances of perforating a blood vessel and of damaging brain tissue, and lowers the risks of brain damage by reducing brain tissue displacement.

U.S. Pat. No. 6,011,996 discloses a lead assembly including a probe, wherein "[t]he length of probe 33, i.e., from the distal-less surface of [macro-] electrode 32 to the microelectrode 34, is suitably in the range of 1 to 10 mm, and preferably about 2-5 mm. The length of this probe is important, as it establishes the distance between the two electrodes . . . . The lead is advanced until the micro-electrode 34 discovers the boundary F of the functional structure . . . . " Since the probe holds the microelectrode extended a fixed distance from the macroelectrode until the microelectrode is withdrawn, the entire assembly (lead with macroelectrode, microelectrode, and probe) must be advanced in order to advance the microelectrode.

U.S. Pat. No. 6,066,165 teaches a lead with "electrode contacts coupled to the lead body at the distal end of the lead. [wherein] the lead body . . . defines a sigma shape." Further, "[t]he sigma segment 20 may as desired be located at any position along the lead body 12 . . . . [However,] each sigma section 20 is formed only of the lead body 12 . . . . " Thus, the lead is made of two sections: the lead body and the electrode(s), and a sigma shape may be positioned only on the lead body portion of the lead. Similarly, in U.S. Pat. No. 5,925,073 "a portion of the lead body located just proximal of the distal electrode 20 is preformed to exhibit a wave-like appearance . . . . "

U.S. Pat. No. 5,843,148 discloses a non-isodiametric chronic DBS lead comprising a "[l]ead body . . . with a diameter typically of about 0.13 cm . . . [and a] distal portion, which carried the ring segment electrodes . . . . The outer diameter D4 of the distal portion . . . is preferably 0.5 mm, but can be in the range of 0.3 to 1.2 mm . . . . " In addition, "[c]ontained within the lead body is a multi-conductor coil 32, each conductor being individually insulated, connecting the pulse generator to respective electrodes carried by the distal end portion of the lead. The lead has a lumen, within coil 32, in which is placed a stylet . . . . " The coil and lumen do not extend into the distal portion of the lead.

U.S. Pat. No. 6,301,492, "provides a microelectrode recording (MER) lead mounted within the central axial channel of a deep brain stimulation lead." The patent states that since "the [deep brain stimulation lead] is implanted through a cannula which is inserted into the brain . . . [the] stylet . . . is somewhat superfluous as the cannula is rigid and provides ample stiffness for effective positioning. The present invention takes advantage of this by mounting the microelectrode recording (MER) lead in the stylet channel, relying on the cannula to provide the requisite rigidity." Similarly, European Patent Application EP 1 062 973 A1 provides "a multifunction electrode device . . . comprising an elongated flexible electrode body having a head section that is provided with a plurality of electrode conductors with associated electrical connections imbedded in the elongated body, wherein a stilette is provided in the elongated body, said stilette comprising an insulating coating around an electrically conductoring [sic] core and an exposed microtip where said tip of the stilette can be advanced through the tip of the electrode body for the performance of microelectrode recordings . . . . The elongated electrode body is provided in an inflexible insertion tube for the insertion of the electrode device to the determined implant position."

A number of cannulas for lead introduction have been proposed, including cannulas that are splittable. Such cannulas include those that are weakened along their length (e.g., via holes or perforations) and/or include a cutting agent (e.g., string or metal strip) allowing them to be torn, ripped, or cut apart for removal. Cannulas and/or cannula systems that can be removed with minimal micro-dislodgment of the lead, and that are simple and inexpensive to manufacture are desired.

FIG. 1A is an axial cross-section view of one embodiment of a lead of the present invention, which lead can be placed using a stylet 100. Stylet 100 may be solid, hollow (i.e., a tube) or other shape (i.e., hexagon, square, oval, etc.), and may be made of stainless steel or similar material. FIG. 1B is an axial cross-section view of another embodiment of a lead that can be placed using stylet 100. The lead may have four independent conductors 104, 105, 106, and 107, as shown in FIGS. 1A and 1B, or depending on the application, may have more or fewer conductors. The conductors of the present invention may have a coating of insulating material, such as ethylene-tetrafluoroethylene (ETFE), polytetrafluoroethylene (PTFE), fluorinated ethylene propylene (FEP), or similar.

In the embodiment of the invention shown in FIG. 1A, conductors 104, 105, 106, and 107 are electrically connected to electrodes 110, 111, 112, and 113, respectively, at the distal end of the lead. In the embodiment of the invention shown in FIG. 1B, conductors 104, 105, 106, and 107 are electrically connected to electrodes 126, 111, 112, and 113, respectively, at the distal end of the lead. As seen in FIG. 1B, electrode 126 is a tip electrode.

As with the conductors, the leads have at least one electrode, and more likely (but not necessarily), have four or more independent electrodes. The electrodes have a surface area in the range of about 1-20 mm$^2$, and are made of an electrode material such as platinum, platinum/iridium, or the like. The electrodes can be cylindrical, semi-cylindrical, circular, semi-circular, or any shape allowing the desired stimulation. The electrodes can be, but are not necessarily, equally spaced so that the electrode array measures around 5-15 mm in length.

The connections between conductors and electrodes are made via crimping, welding, a combination of these, or other suitable means. At the proximal end of the lead, the conductors 104, 105, 106, and 107 are electrically connected to contacts 116, 117, 118, and 119, via crimping, welding, a combination of these, or other suitable means. These contacts are used to electrically connect the lead to a device that generates stimulation pulses, which pulses are delivered via the electrodes. Alternatively, the contacts may make an electrical connection to intermediate wiring such as a temporary cable.

The lead shown in FIG. 1A has a soft, rounded distal tip 124 made of a biocompatible, insulating polymer, such as silicone, polyurethane, or epoxy. A soft, rounded distal tip made of a polymer may reduce the risk of tissue damage during lead introduction. This same polymer may be used for the body 128 of the lead. In contrast, the lead shown in FIG. 1B has a semi-circular electrode 126 on the distal tip. Electrodes such as semi-circular tip electrodes have different current and density distributions than cylindrical electrodes, and so are preferred by some physicians. Also, a lead with a tip electrode may not need to be advanced as far into the tissue as a lead with "non-functional" material at the tip. The outer diameter of the leads of FIGS. 1A and 1B is preferably, but not necessarily, less than about 1.5 mm (0.060 inch), for instance, less than about 1.25 mm (0.050 inch), or even less than about 1 mm (0.040 inch).

FIGS. 2A, 2B, and 2C show additional lead embodiments. These leads have a lumen and through-hole 132 that allow for lead placement over a recording microelectrode wire 134, which may be comprised of one or more electrodes. In addition, the lead may be introduced through the same cannula that accommodates the recording microelectrode. The outer diameter of the leads of FIGS. 2A, 2B, and 2C is preferably similar to that previously stated for leads of FIGS. 1A and 1B.

In some arrangements, microelectrode wire 134, or a portion of microelectrode wire 134, is coated with insulating compound, such as glass, parylene, or epoxylite, leaving only a very small electrode surface area 139 (e.g., about 0.01 to 1000 μm$^2$) exposed. This configuration increases impedance, which is helpful for single cell recording. As shown in FIGS. 2C-2F, microelectrode wire 134 (not shown in FIGS. 2D and 2E) and surface area 139 are preferably, but not necessarily, part of a recording microelectrode 135.

Around the microelectrode wire, for instance, a coated microelectrode wire, is an electrode tube 136 of stainless steel or similarly strong material. Electrode tube 136 is preferably, but not necessarily, situated within electrode insulation 138 made of, e.g., polyimide or the like. Recording microelectrode 135 preferably, but not necessarily, has a total diameter of about 0.28-0.56 mm (0.011-0.022 inch), such as about 0.43-0.46 mm (0.017-0.018 inch) or less.

Conductor winding 140 (wound in helical fashion) forms a lumen 141, allowing a protective tube 130 and microelectrode 135 passage through the length of the lead. Insulation 142 surrounds conductor winding 140, and extends from the proximal end of the lead to nearly the distal tip of the lead. Conventional biocompatible insulating material, such as silicone or polyurethane or the like, may be used as insulation 142.

At the distal end of the lead is a tip 144, which may be an electrode, insulating material, or both. Tip 144 may have a countersunk feature 146 (shown in FIG. 2C), which stops and centers protective tube 130, if used, making protective tube 130 (which may also act as a stylet) self-aligning. If tip 144 contains insulating material, the material may be the same as for insulation 142, or is a material with a higher durometer, such as 75D polyurethane or epoxy equivalent or the like, to provide resistance to protective tube 130 pushing against it.

FIG. 2F shows microelectrode 135 advanced beyond the distal tip 144 of the lead 128. The ability to independently slide microelectrode 135 and protective tube 130 allows the lead 128 and microelectrode 135 to be advanced and retracted in relation to one another. Alternatively, protective tube 130 may be held in place, or may be eliminated.

FIG. 3 shows yet another embodiment of a lead, in cross-section view. The lead of FIG. 3 does not have a lumen for passage of a stylet or recording microelectrode. Instead, the lead has smaller lumens 150, for accommodating independent cable conductors 154, which are used rather than conventional single-strand wire conductors. As with other embodiments, the body 128 of the lead may be made of commonly used biocompatible insulating material, such as silicone or polyurethane or the like, and may also be isodiametric. The lead of FIG. 3 may be placed with a cannula, as one unit.

A configuration as described above allows a lead to have a smaller diameter since a lumen for the stylet is not required. Therefore, a smaller cannula may be used to place the lead, and thus a smaller hole made through the tissue. The risk of perforating a blood vessel, or damaging other tissue, is less with a smaller hole. Also, a smaller lead displaces less tissue, and this further reduces the risk of tissue damage, such as brain damage. The outer diameter of the isodiametric lead of FIG. 3 may be less than about 1.25 mm (0.050 inch), for instance, less than about 1 mm (0.040 inch), or even less than about 0.50 mm (0.020 inch).

The lead and lead introduction system embodiments of the present invention may be made via standard techniques known by those of ordinary skill in the art, and may lead to one or more of the following, among other things:

1. a reduced number of procedural steps, since one cannula is used for placing both the recording microelectrode and the lead;
2. no need to place a stimulating macroelectrode, since the lead performs the function of the macroelectrode;
3. chronic implantation of the electrode(s) used during stimulation testing; and
4. elimination of the risk of failing to get the electrodes of the lead to the same location as the microelectrode (usually caused by insertion of a different cannula for lead placement).

The traditional procedures described earlier for implanting a permanent brain stimulating or DBS lead, may thus be modified to involve fewer steps, which generally include the following.

1. Place the stereotactic frame on the subject.
2. Perform MRI or equivalent imaging of subject with stereotactic frame.
3. Identify a theoretical target using planning software.
4. Place subject with stereotactic frame in head rest.
5. Cut skin flap, exposing working surface area of cranium using scalp clips.
6. Place stereotactic arc with target coordinate settings and identify location on skull for creation of burr hole.
7. Remove arc and drill a burr hole in the patient's skull.
8. Place the base of the lead anchor.
9. With the microelectrode recording drive attached, and with the appropriate stereotactic frame adaptor inserted into the instrument guide, place the stereotactic arc.
10. Insert an insertion cannula and rod into the brain until they are approximately 25 mm above the target.
11. Remove the insertion rod, leaving the cannula in place.
12. Insert a lead and recording microelectrode, with the tip of the microelectrode flush with the tip of the lead.
13. Attach a connector pin of the recording microelectrode to the microelectrode recording system.
14. Starting approximately 25 mm above the target, begin the microelectrode recording tract using the microdrive to advance the microelectrode at a specified rate.
15. If the target is identified, proceed to step 16. If the target is not identified, proceed with the following:
    a. Using the recording results and the pre-operative imaging, determine a new set of coordinates for the theoretical target.
    b. Disconnect the recording microelectrode from the microelectrode recording system.
    c. Remove the recording microelectrode, lead and cannula.
    d. Adjust the coordinates of the stereotactic frame.
    e. Continue at step 10, above.
16. Advance the lead such that the tip of the microelectrode and the tip of the lead are flush.
17. Connect the proximal end of the lead to the distal end of the External Trial Stimulator (ETS) test cable and connect the proximal end of the ETS test cable to the ETS.
18. Perform the desired stimulation and measurements using any one or combination of four electrodes on the lead.
19. If the results are favorable, proceed to step 29. If the results are not favorable, proceed with the following:
    a. Using the recording results and the pre-operative imaging, determine a new set of coordinates for the theoretical target.
    b. Disconnect the recording microelectrode from the microelectrode recording system.
    c. Remove the recording microelectrode, lead and cannula.
    d. Adjust the coordinates of the stereotactic frame.
    e. Continue at step 10, above.
20. Remove the cannula and microelectrode in the order that will be apparent to the physician.
21. Lock the DBS lead in the lead anchor.

Some physicians might use additional steps, fewer steps, and/or perform the steps in a different order. Obviously, many of these steps cannot be avoided. However, it is also obvious that many of the steps previously required are no longer necessary, using the teachings of the present invention.

Figure 4A:
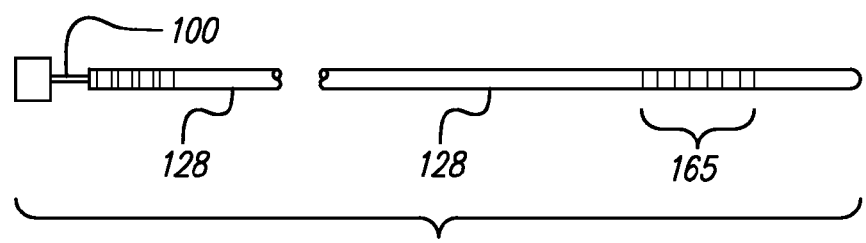
FIG. 4A depicts an embodiment of a lead of the present invention with a stylet inserted into the lead.
Figure 4B:
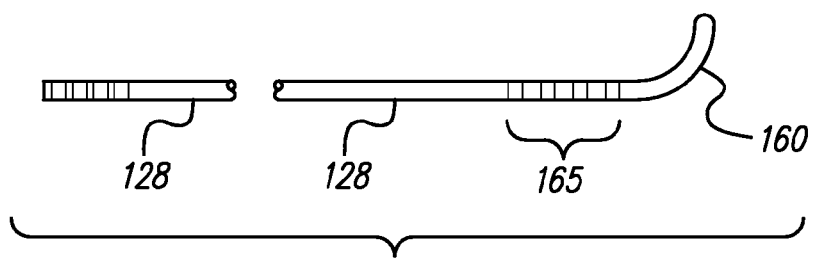
FIGS. 4B-4H depict various configuration of leads of the present invention, with stylet removed.
Figure 4C:
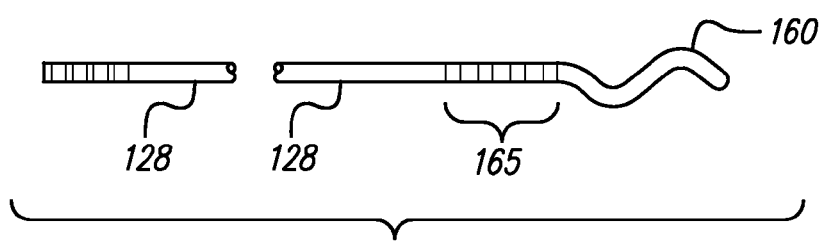
Figure 4D:
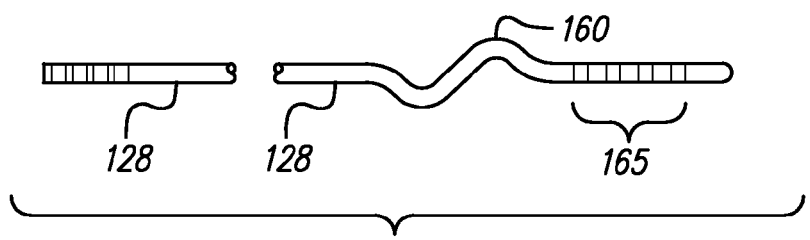
Figure 4E:
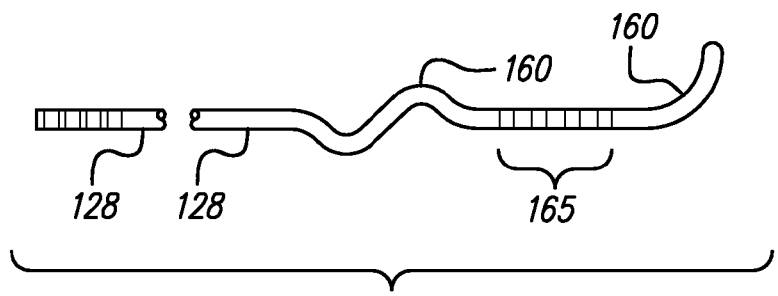
Figure 4F:
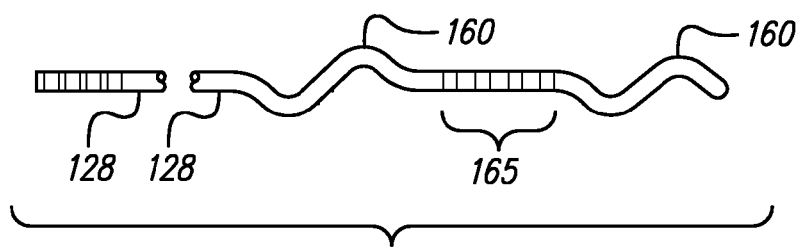
Figure 4G:
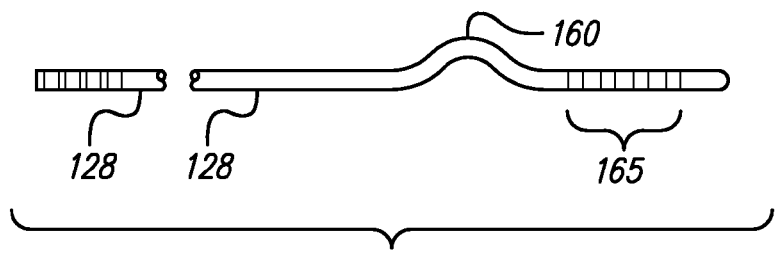
Figure 4H:
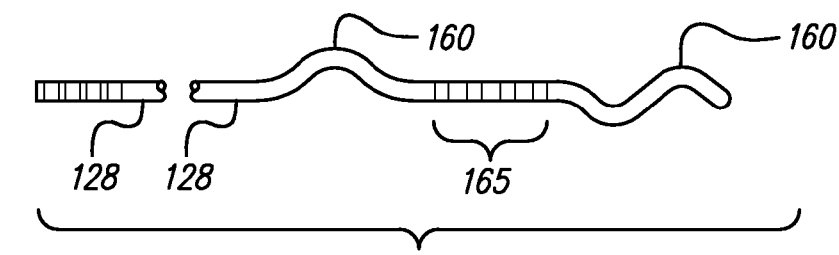

A lead may also be formed with a shape that enhances lead stability. When a stylet 100 is fully inserted into a lead as shown in FIG. 4A, the lead is essentially straight. As stylet 100 is removed from the lead, a pre-formed lead shape, as in one of FIGS. 4B-4H, may appear. Similarly, when recording microelectrode 135 and protective tube 130 are removed from the lead, or a cannula is removed from over the lead, the pre-formed shape of the lead appears. Alternatively, due to insertion into certain tissue, the lead may remain essentially straight, in which case the preformed shape will likely provide stabilizing force.

Lead shapes as in FIGS. 4B-4H result from forming the insulation of lead body 128. In the case of a thermoset insulation material, such as silicone rubber, the tubing may be molded into the pre-formed shape while the thermoset is in a green (uncured) state. In the case of a thermoplastic insulation material, such as polyurethane, the tubing may be molded into the pre-formed shape before, during, or after lead assembly, depending on the materials of the lead components, and the temperature required to shape the insulation being used.

As stated above, FIGS. 4B-4H show various pre-formed shapes that can enhance lead stability. A pre-formed stability feature 160 may be distal, proximal, or both distal and proximal to electrode array 165, and is preferably, but not necessarily, made of the same material as body 128. A stability feature distal to the electrode array may reduce the risk of the electrode array moving during cannula withdraw more than if the feature was proximal to the electrode array. When a curved stability feature is provided both distal and proximal to the electrode array, the electrode array is stabilized on both sides, helping to minimize movement. In addition, the distal curve may help stabilize the lead as the cannula is removed over the proximal curve.

FIGS. 4B-4H show pre-formed shapes consisting of a single direction curve or a bi-directional curve. A potential advantage of a bi-directional curve is that the lead is better aligned with the vertical axis. To control the force exerted by the curve(s), the amplitude, spacing, material, and cross-sectional dimensions of the pre-formed curve can be adjusted. In addition, all or some electrodes of electrode array 165 may be positioned on a stability feature 160. Theoretical and experimental analysis and testing may be required to determine what, if any, curve/electrode configuration is ideal for optimum non-traumatic stabilization of the lead.

Figure 5:
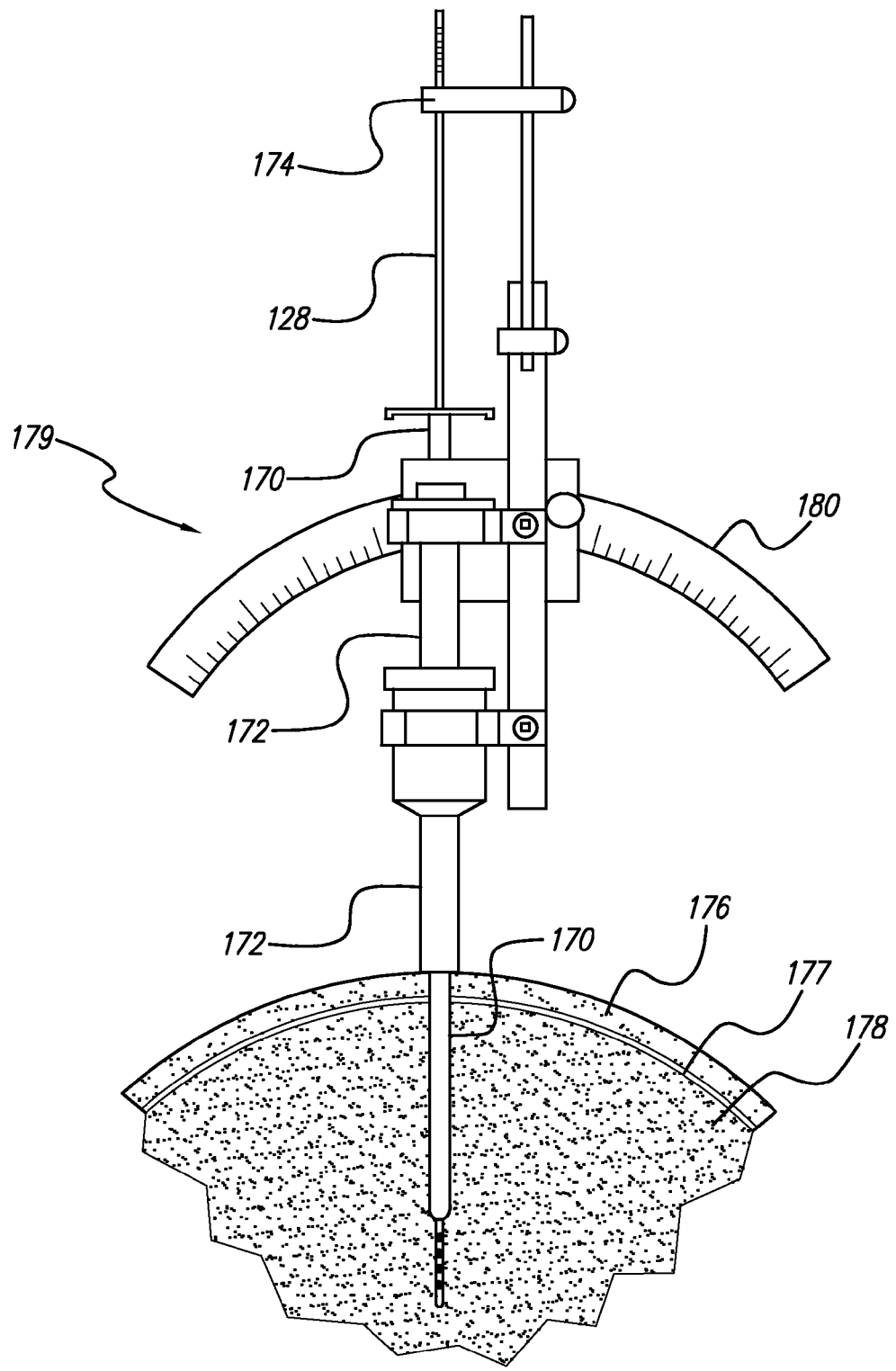
FIG. 5 is one embodiment of a cannula system of the present invention.

As mentioned earlier, another potential item in the lead implant procedure is the cannula that may be used to guide and support the lead during implantation. FIG. 5 shows a lead introduction system with an inner cannula 170 and an outer cannula 172. Inner cannula 170 is used to guide the lead into the body tissue. Stabilization of the proximal end of lead 128 is provided with an optional clamp or holder 174, which may also include lead attachments used for stimulation and/or recording. Outer cannula 172 is suitably affixed to stereotactic frame 179, and is used to stabilize lead 128 and inner cannula 170 between the skull 176 and stereotactic arc 180.

This, in turn, may provide better stability and control of inner cannula 170 as it travels through the dura mater 177 and brain 178. Outer cannula 172 can be used to support various inner cannulas, e.g., a cannula for placing a recording microelectrode or stimulating macroelectrode and/or a cannula for placing a lead. This system minimizes the risk of losing the target stimulation site when changing cannulas.

FIGS. 6A-6E demonstrate one embodiment of inner cannula 170, and a method for removing it. In this embodiment, inner cannula 170 is splittable, and may, as shown, have handles 182 at the proximal end. As handles 182 are pulled up and away from each other, inner cannula 170 splits along a perforated, or similarly splittable interface, from the proximal end toward the distal end, as shown in FIGS. 6A-6E. Outer cannula 172 stabilizes the lead during removal of the splittable inner cannula 170.

In a related configuration, the sections of inner cannula 170 are held together with a biocompatible glue or the like that breaks when a force is applied to the cannula. In another embodiment, the sections of inner cannula 170 are held together with a clamp or other locking mechanism at the proximal end. In yet another configuration, inner cannula 170 has two sections with a mating wall configuration, similar to a jigsaw puzzle, allowing one half to be slidably removed at a time, which reduces the chance of dislodging the lead during inner cannula removal.

In another embodiment, inner cannula 170 has slidable sections. In one configuration, the slidable sections are held together by the force of outer cannula 172, which force can be reduced to allow removal of inner cannula 170. For instance, outer cannula 172 may have a slit along its length, which may be widened and narrowed by, e.g., turning a thumbscrew. This allows inner cannula 170 to be removed in sections from within outer cannula 172.

Figure 7A:
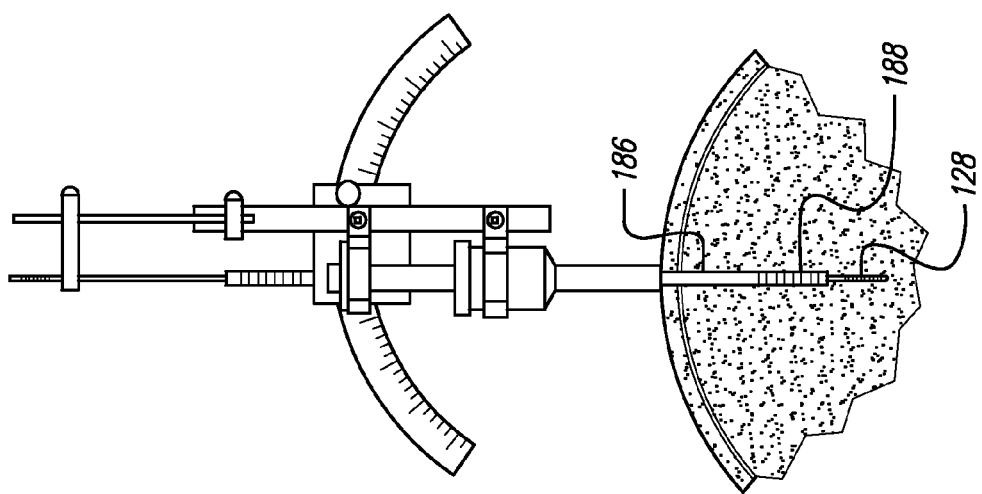
FIGS. 7A-7B show yet another embodiment of a cannula system of the present invention.
Figure 7B:
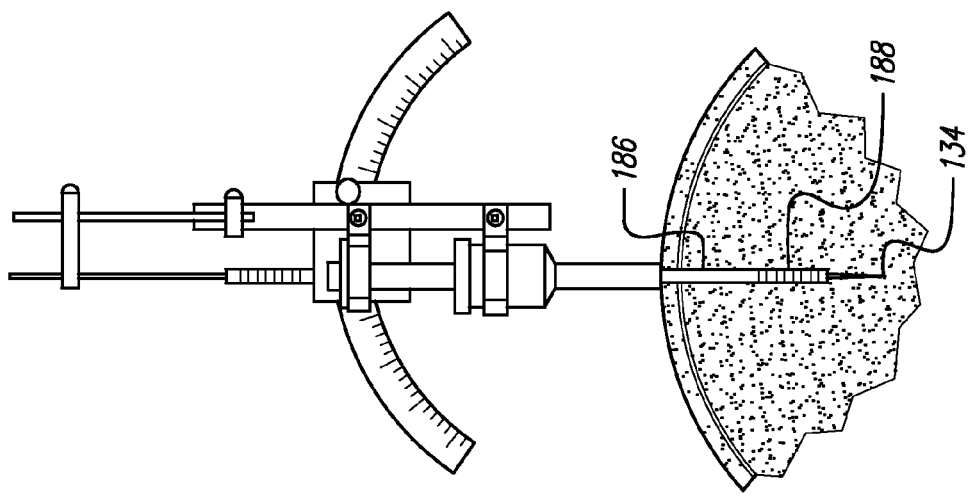

FIGS. 7A and 7B show another embodiment of an inner cannula. Cannula 186 has incorporated stimulating macroelectrode(s) 188. FIG. 7A shows cannula 186 and recording microelectrode wire 134 in the brain. FIG. 7B shows cannula 186 and lead 128 in the brain. This embodiment of cannula 186 may include one or more of the following aspects, among other things:

1. when the appropriate stimulation site is located with the recording microelectrode, the stimulating macroelectrodes 188 are in place and ready to deliver test stimulation pulses;
2. stimulating macroelectrodes 188 may be advanced over the recording microelectrode to the exact same anatomical location as the microelectrode;
3. lead 128 may be advanced inside cannula 186 to the exact same location as stimulating macroelectrodes 188;
4. only one cannula insertion is required;
5. only one "change-out" of devices inside the cannula is required;
6. bipolar recording/stimulation is possible.

Cannula 186 may be splittable, peelable, slidable, or the like, or may be configured as described in any of the above embodiments, but this is not required.

While the invention herein disclosed has been described by means of specific embodiments and applications thereof, numerous modifications and variations could be made thereto by those skilled in the art without departing from the scope of the invention set forth in the claims. For instance, a variety of shapes may be used as a lead stabilizing feature, such as angled features. In another variation, the stabilizing features may project from a straight lead, rather than the lead itself forming the stabilizing feature. In addition, various lead designs and lead introduction tools of the present invention may be used for deep brain stimulation, or may be used for stimulating other areas of the body or for introducing chronic or temporary leads, catheters, or similarly shaped devices to other locations throughout the body. As such, the word "lead" comprises various types of leads, catheters, and similarly shaped devices.

What is claimed is:

1. A method of implanting a brain stimulating lead, consisting essentially of:
    identifying a theoretical target for brain stimulation;
    creating a point of entry into the brain;
    inserting a lead and a microelectrode into the brain to a position above the theoretical target;
    advancing the microelectrode toward the theoretical target to locate a stimulation target;
    advancing the lead to the stimulation target located by the microelectrode;
    performing test stimulation with the lead to confirm location of the stimulation target;
    removing the microelectrode; and
    securing the lead,
    wherein inserting the lead and the microelectrode comprises,
        holding a first cannula in a substantially fixed position external to the body;
        slidably supporting a second cannula with the first cannula;
        positioning the second cannula with a proximal end extending beyond the proximal end of the first cannula and a distal end extending beyond the distal end of the first cannula and into the body;
        inserting the lead and the microelectrode through the second cannula; and
        pulling the second cannula away from the patient's brain.

2. The method of claim 1 wherein at least one of identifying the theoretical target, creating the point of entry, inserting the lead and the microelectrode, advancing the microelectrode, and advancing the lead comprises using a stereotactic frame.

3. The method of claim 1, wherein the second cannula includes at least two splittable sections having a perforated interface.

4. The method of claim 3, wherein pulling the second cannula away from the patient's brain further includes, removing at least one splittable section at a time.

5. The method of claim 3, wherein the second cannula includes at least one handle at the proximal end.

6. The method of claim 5, wherein the at least one handle is adapted to be pulled up and away from the patient's brain separating the second cannula along the perforated interface.

7. The method of claim 3, wherein the second cannula includes a macroelectrode attached to the distal end of the second cannula.

* * * * *